United States Patent [19]

Chiang

[11] Patent Number: 5,256,689
[45] Date of Patent: Oct. 26, 1993

[54] CHOLESTEROL LOWERING COMPOUNDS

[75] Inventor: Yuan-Ching P. Chiang, Scotch Plains, N.J.

[73] Assignee: Merck & Co., Inc., Rahway, N.J.

[21] Appl. No.: 966,764

[22] Filed: Oct. 26, 1992

Related U.S. Application Data

[63] Continuation-in-part of Ser. No. 866,749, Apr. 15, 1992, which is a continuation-in-part of Ser. No. 805,602, Dec. 9, 1991, which is a continuation-in-part of Ser. No. 698,766, May 10, 1991, abandoned.

[51] Int. Cl.$^5$ ................. A61K 31/335; C07D 319/04
[52] U.S. Cl. .................................. 514/452; 549/363; 549/328; 549/318; 549/310; 549/292; 549/271; 549/270; 549/230; 549/228; 514/450
[58] Field of Search ............... 549/363, 328, 310, 292, 549/285, 318, 271, 270, 230, 228; 514/452, 450

[56] References Cited

U.S. PATENT DOCUMENTS

| | | |
|---|---|---|
| 5,026,554 | 6/1991 | Bartizal et al. |
| 5,053,425 | 10/1991 | Bartizal et al. |
| 5,055,487 | 10/1991 | Bartizale et al. |
| 5,096,923 | 3/1992 | Bergstrom et al. |
| 5,102,907 | 4/1992 | Bergstrom et al. |
| 5,132,320 | 7/1992 | Bergstrom et al. |

FOREIGN PATENT DOCUMENTS

| | | |
|---|---|---|
| 0448393 | 9/1991 | European Pat. Off. |
| 0450812 | 10/1991 | European Pat. Off. |
| 0475706 | 3/1992 | European Pat. Off. |
| 0494622 | 7/1992 | European Pat. Off. |
| 0503520 | 9/1992 | European Pat. Off. |
| 0512865 | 11/1992 | European Pat. Off. |
| WO 92/12156 | 1/1992 | PCT Int'l Appl. |
| WO 92/12157 | 1/1992 | PCT Int'l Appl. |
| WO 92/12158 | 1/1992 | PCT Int'l Appl. |
| WO 92/12159 | 1/1992 | PCT Int'l Appl. |
| WO 92/12160 | 7/1992 | PCT Int'l Appl. |

OTHER PUBLICATIONS

Poulter et al., *J. Med. Chem. Soc.*, 111, 3734–9 (1989).
Corey et al., *J. Med. Chem. Soc.*, 98, 1291–3 (1976).
Ortiz de Montellano, *J. Med. Chem.*, 20, 243–9 (1977).
Dawson et al., *J. Antibiotics*, 45, 639–47 (1992).
Sidebottom et al., *J. Antibiotics*, 45, 648–58 (1992).
Jones et al., *J. Antibiotics*, 45, 1492–98 (1992).
Baxter et al., *J. Biol. Chem.* 267, 11705–08 (1992).

*Primary Examiner*—Nicky Chan
*Attorney, Agent, or Firm*—Charles M. Caruso; Melvin Winokur; Carol S. Quagliato

[57] ABSTRACT

Disclosed herein are compounds of structural formula (I)

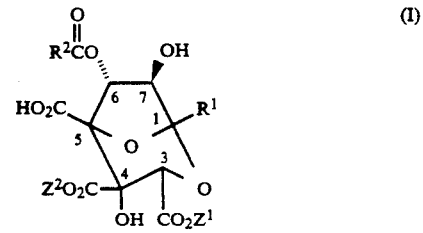

which are useful as cholesterol lowering agents and as inhibitors of squalene synthase.

10 Claims, No Drawings

CHOLESTEROL LOWERING COMPOUNDS

This application is a continuation-in-part of co-pending U.S. Ser. No. 07/866,749, filed Apr. 15, 1992, which itself is a continuation-in-part of co-pending U.S. Ser. No. 07/805,602, filed Dec. 9, 1991, which itself is a continuation-in-part of co-pending U.S. Ser. No. 07/698,766, filed May 10, 1991 now abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin) and ZOCOR ® (simvastatin), now commercially available, are members of a group of very active antihypercholesterolemic agents that function by limiting cholesterol biosynthesis by inhibiting the enzyme, HMG-CoA reductase.

Squalene synthase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analogs containing compounds such as those described in P. Ortiz de Montellano, et al., *J. Med Chem.*, 20, 243 (1977) and E. J. Corey and R. Volante, *J. Am. Chem. Soc.*, 98, 1291 (1976). S. Biller (U.S. Pat. No. 4,871,721) describes isoprenoid (phosphinylmethyl)phosphonates as inhibitors of squalene synthase.

Recently certain nonphosphorous containing inhibitors of squalene synthase have been isolated as natural products. These natural product inhibitors are described in U.S. Pat. Nos. 5,102,907; 5,132,320; 5,096,923; 5,026,554; 5,055,487; and 5,053,425. A need still remains for a more effective squalene synthase inhibitor, i.e. one that provides a greater antihypercholesterolemic effect and exhibits a good safety profile.

The present invention is directed to semi-synthetic analogs of the above-noted natural products, and a novel process for making them.

DETAILED DESCRIPTION OF THE INVENTION

This invention relates to compounds of structural formula (I) which are useful as cholesterol lowering agents:

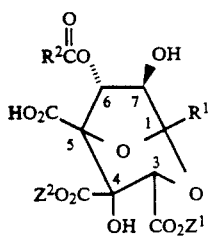

(I)

wherein:

$R^1$ is (1)

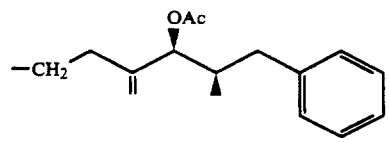

or (2)

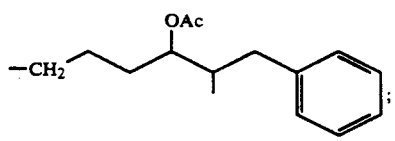

$R^2$ is (1)

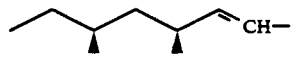

or (2)

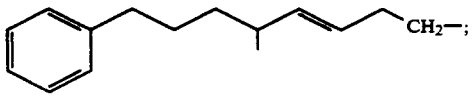

$Z^1$ is $C_{1-3}$alkyl or $-CH_2-CH=CH_2$;

$Z^2$ is (1)

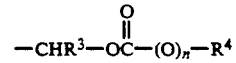

wherein
$R^3$ is —H or $C_{1-4}$alkyl,
n is zero or 1, and
$R^4$ is
  a) $C_{1-5}$ alkyl,
  b) phenyl, or
  c) phenyl substituted with X and Y, defined below,
or, when $R^3$ is $C_{1-4}$ alkyl, $R^3$ and $R^4$ are joined together to form a monocyclic or bicyclic ring system,
or, $R^4$ is joined together with the carbon to which $R^3$ is attached to form a monocyclic or bicyclic ring system, and $R^3$ represents the bond between $R^4$ and the carbon to which $R^3$ is attached, (2)

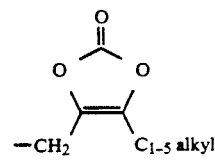

or (3)

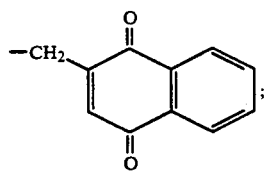

and

X and Y are each independently selected from:
(1) hydrogen,
(2) hydroxy,
(3) halogen,
(4) trifluoromethyl,
(5) $C_{1-4}$alkyl,
(6) $C_{1-4}$alkyl—O—,
(7) $C_{1-4}$alkyl—C(O)—O—,
(8) —$CO_2C_{1-4}$alkyl,
(10) —$CO_2H$, and
(11) nitro;

or a pharmaceutically acceptable salt thereof.

Preferred compounds of this invention are depicted in Tables 1 and 2, below.

TABLE 1

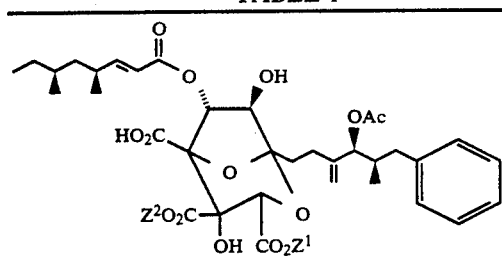
(II)

| | $Z^1$ | $Z^2$ |
|---|---|---|
| 1a) | $CH_3$ | —$CH_2OC(O)$—$C(CH_3)_3$ |
| 1b) | —$CH_2CH_3$ | —$CH_2OC(O)$—$C(CH_3)_3$ |
| 1c) | —$CH_2CH_2CH_3$ | —$CH_2OC(O)$—$C(CH_3)_3$ |
| 1d) | —$CH_2$—$CH=CH_2$ | —$CH_2OC(O)$—$C(CH_3)_3$ |
| 1e) | —$CH(CH_3)_2$ | —$CH_2OC(O)$—$C(CH_3)_3$ |
| 1f) | —$CH_2CH_3$ | —$CH(CH_3)OC(O)$—$OCH_2CH_3$ |
| 1g) | —$CH_2CH_2CH_3$ | —$CH(CH_3)OC(O)$—$OCH_2CH_3$ |
| 1h) | —$CH_2CH_3$ | —$CH(CH_3)OC(O)$—$C(CH_3)_3$ |
| 1i) | —$CH_2CH_2CH_3$ | —$CH(CH_3)OC(O)$—$C(CH_3)_3$ |

TABLE 1-continued (II structure)

| | $Z^1$ | $Z^2$ |
|---|---|---|
| 1j) | —$CH_2CH_3$ | (phthalide-CH-CH₃ group) |
| 1k) | —$CH_2CH_2CH_3$ | (phthalide-CH-CH₃ group) |
| 1l') | —$CH_2CH_3$ | —$CH_2$-(methyl dioxolenone) |
| 1m) | —$CH_2CH_2CH_3$ | —$CH_2$-(methyl dioxolenone) |

TABLE 2

(III structure)

| | $Z^1$ | $Z^2$ |
|---|---|---|
| 2a) | —$CH_2CH_3$ | —$CH_2$—$OC(O)$—$C(CH_3)_3$ |
| 2b) | —$CH_2CH_2CH_3$ | —$CH_2$—$OC(O)$—$C(CH_3)_3$ |

Except where specifically defined to the contrary, the word "alkyl" includes both branched and straight chain saturated aliphatic hydrocarbon groups having the specified number of carbon atoms, such as, e.g., methyl (Me), ethyl (Et), iso-propyl (i-Pr), and tert-butyl (t-Bu). Acyl, i.e. —$COCH_3$, is abbreviated herein as "Ac", phenyl is "Ph", and ethyl acetate is "EtOAc."

The compounds of formula I can be prepared from (1S, 3S, 4S, 5R, 6R, 7R)-1-[(4S)-acetoxy-3-methylene-5-methyl-6-phenyl]hexyl-4,6,7-trihydroxy-6-0-(4,6- dimethyl-2-octenoyl)-2,8-dioxabicylco[3.2.1]octane-3,4,5-tricarboxylic acid (referred to herein as compound IA), or (1S, 3S, 4S, 5R, 6R, 7R)-1-[(4)-acetoxy-5-methyl-6-phenyl]hexyl-4,6,7-tri-hydroxy-6-0-(6-methyl-9-phenyl-4-nonenoyl)-2,8-dioxabicyclo[3.2.1]-octane-3,4,5-tricarboxylic acid (referred to herein as compound IC) according to the sequences described in Schemes A, B and C. The preparation of the starting materials, IA and IC, are described in U.S. Pat. Nos. 5,096,923 and 5,102,907, respectively. Although Schemes A–C depict the use of compound IA and derivatives thereof, the same methods can be used employing compound IC and its derivatives. Furthermore, scheme C, as well as schemes A and B, can be used to make the compounds of the invention, but can also be used by one skilled in the art to synthesize a broader range of C-3, C-4 diester products. For example, one could use starting materials with a broader range of $R^1$ and $R^2$ groups and/or having an ether at the 7-position, or one could use other appropriate alcohols, alkyl halides, etc., to form a variety of esters at the C-3, C-4 and C-5 positions using the described methods.

Compounds are named in the examples and in some places throughout the description as ester derivatives at the C3, C4 and/or C5 carboxylic acid positions of compounds IA and IC as, e.g., IA-3-ethyl-4-pivaloyloxymethyl diester (compound II in Table 1 wherein $Z^1$ is ethyl and $Z^2$ is pivaloyloxymethyl), and IC-3-n-propyl ester (compound III in Table 2 wherein $Z^1$ is n-propyl and $Z^2$ is —H).

SCHEME A

C-3 monoesters (1) could be prepared by several procedures. Stirring IA in an alcohol of formula $Z^1$—OH, wherein $Z^1$ is defined above, in the presence of an acid such as sulfuric acid or hydrochloric acid that can be added or generated in situ by the addition of acetylchloride to the alcohol solvent used, gives selective esterification at C-3 to produce (1). IA-3,4-diesters (IIA) can be prepared from C-3 monoesters (1) by stirring a C-3 monoester (1) with a base such as 1,8-diazabicyclo[5.4.0]undec-7-ene (DBU) and an appropriate alkyl halide of formula $Z^2$—X, wherein X is a halide such as —Cl, —Br, or —I and $Z^2$ is defined above, in a solvent such as benzene, tetrahydrofuran (THF) or acetonitrile. This reaction condition also produces the C-3,C-5-diesters and the C-3,C-4,C-5-triesters of IA which can be separated by chromatographic methods such as preparative thin layer chromatography on silica gel using solvents such as methylene chloride and acetone with small amounts of acetic acid added (a typical ratio would be 88/8/4 $CH_2Cl_2$/acetone/acetic acid by volume) or by preparative high pressure liquid chromatography on reverse-phase packing such as Zorbax RX C8 eluting with a gradient solvent system beginning with acetonitrile/water (1:1 with 0.005% trifluoroacetic acid) and increasing eluting power to 100% acetonitrile (with 0.005% trifluoroacetic acid). In this reaction, using one equivalent of base to substrate ratio mainly gives the C-3, C-4-diesters, while a base to substrate ratio of two or more gives mainly the C-3,C-5-diesters or C-3,C-4,C-5-triesters as the major product.

SCHEME B

When the C-3 monoesterification in Scheme A is carried out in benzyl alcohol, the C-3 benzyl ester (2) formed can be used as a C-3 protecting group. This allows modification of the C-4 and C-5 carboxyl groups to produce (3) by forming esters in these positions with an isourea reagent such as O-t-butyl-N,N'-diisopropylisourea. [Mathias, L. J., Synthesis, 561–576 (1979)]. IA-4,5-di-t-butyl diester (4) can be prepared from IA-3-benzyl-4,5-di-t-butyl ester (3) by removing the benzyl group by hydrogenolysis with Pd/C and hydrogen gas or transfer hydrogenolysis with Pd/C and methyl cyclohexadiene. IA-4,5-di-t-butyl diester (4) can be modified at the C-3 position by several procedures. For example, IA-4,5-di-t-butyl diester (4) could be treated with N-methyl morpholine followed by isobutylchloroformate to form a mixed anhydride which reacts well with various alcohols to form the corresponding IA-3-$Z^1$-4,5-di-t-butyl triesters (5). IA-4,5-di-t-butyl diester (4) could also be treated with coupling reagents such as carbonyl diimidazole, thionyl chloride, benzotriazol-1-yloxytris(dimethylamino)phosphonium hexafluorophosphate (BOP reagent) or any of the other standard coupling reagents known to those skilled in the art, such as dicyclohexylcarbodiimide (DCC) or 2-ethoxy-1-ethoxycarbonyl-1,2-dihydroquinolone (EEDQ), followed by an alcohol to form esters (5). Also IA-4,5-di-t-butyl diester (4) can be converted to the triester (5) by stirring with an $Z^1$O-N,N'-dialkyl-isourea in a solution such as toluene, benzene, acetonitrile, tetrahydrofuran (THF) and/or dimethoxyethane (DME). [Mathias, L. J., Synthesis, 561–576 (1979)]. The C-4,C-5-di-t-butyl ester groups could be removed later by stirring the triester (5) formed with trifluoroacetic acid (TFA) in methylene chloride to form (1). The C-3 monoesters (1) thus produced may be transformed into the C-3,C-4-diesters (IIA) as described in Scheme A.

SCHEME C

As an alternative to the method of Scheme B, the triester (5) can be selectively saponified at the C-4 position by action of certain Lewis acids such as thionyl chloride, tin(IV) chloride or hydrogen fluoride. A catalytic amount of tin(IV) chloride is used for the saponification, e.g. between 0.05 to 0.5 equivalents per one equivalent of triester (5), with stirring at room temperature for about one to twenty hours; 0.05 equivalents of tin(IV) chloride with stirring for 18 to 20 hours is preferred. An excess of thionyl chloride is used to saponify the triester (5), e.g., from about 40 to 60 equivalents of thionyl chloride per one equivalent of (5), and the reaction is stirred for about 3 to 4 days at room temperature. When hydrogen fluoride is used in this step, a large excess of hydrogen fluoride, e.g. about 350 to 400 equivalents, is used per one equivalent of (5), and the reaction is stirred for about 8 hours to obtain the diester (6). This provides a C-3,C-5 diester (6) that can be esterified at the 4-carboxylic acid to form the IA-3-$Z^1$-4-$Z^2$-5-t-butyl triester (7) by treatment with one equivalent each of DBU and an alkyl halide per equivalent of diester (6), as described in Scheme A. The C-3, C-5 diester (6) may also be esterified at the 4-carboxylic acid by using the procedures described in Scheme B for producing the triester (5) from the C-4, C-5-di-t-butyl diester (4). Such esterification procedures include treatment of (6) with one equivalent each of N-methyl morpholine and isobutylchloroformate to form a mixed anhydride followed by treatment with from one to five equivalents of an alcohol of formula $Z^2$—OH per equivalent of (6); treatment of (6) with one equivalent of a coupling reagent and one equivalent of the alcohol $Z^2$—OH per equivalent of (6); or treatment of (6) with one to three equivalents of a $Z^2O$—N,N'-dialkyl-isourea per equivalent of (6).

The triester (7) may be purified by flash chromatography on silica gel using solvents such as ethyl acetate and methylene chloride. The purified triester (7) may be deprotected by stirring with trifluoroacetic acid (TFA) in methylene chloride to give the compounds of this invention (IIA). The triester (5) can be made via the route shown in Scheme B, or alternatively it can be prepared by reacting compound (1) with t-butyl-O-N,N'-diisopropylisourea. Compound (1) is prepared via the method shown in Scheme A.

SCHEME A

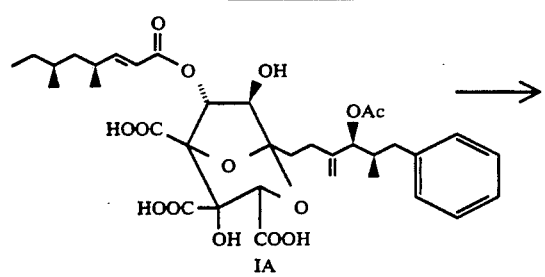

IA

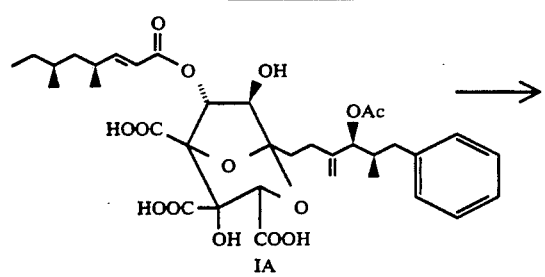

1

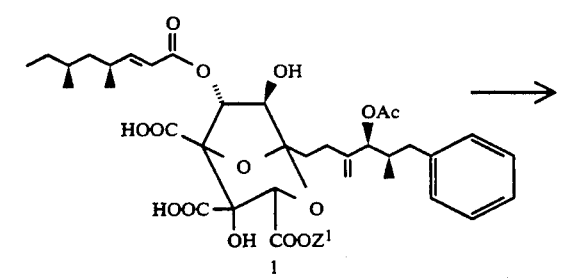

IIA

SCHEME B

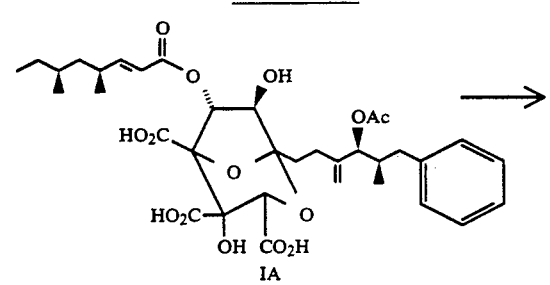

IA

-continued
SCHEME B

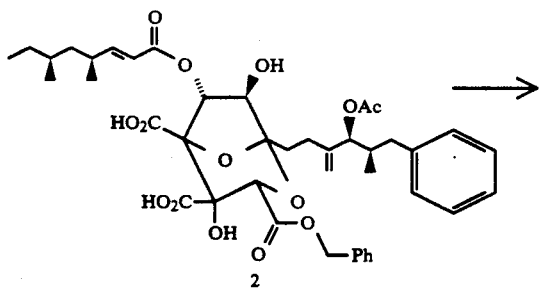

2

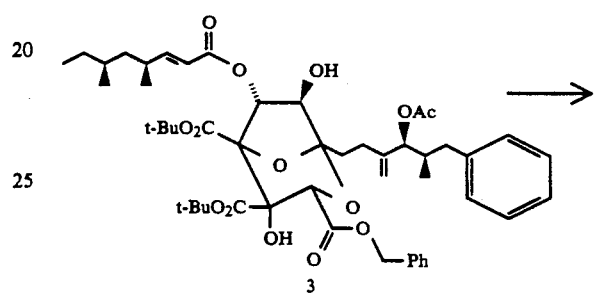

3

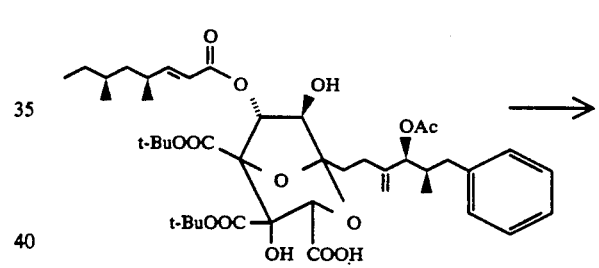

4

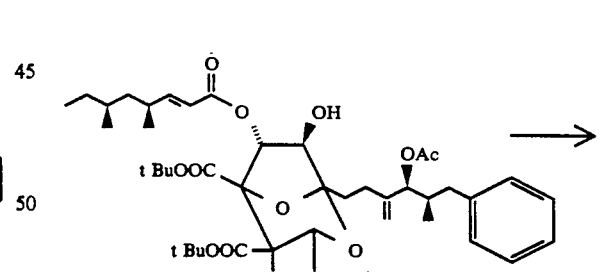

5

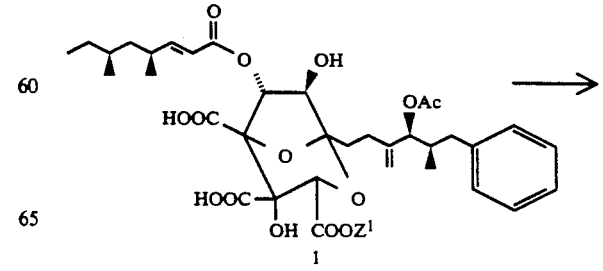

1

-continued
SCHEME B

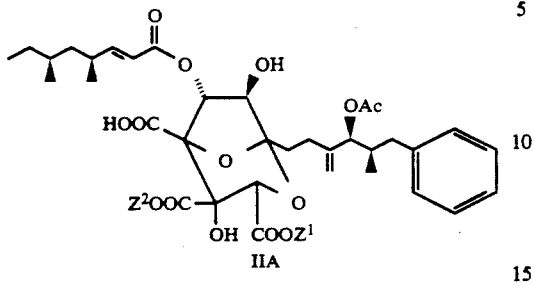
IIA

SCHEME C

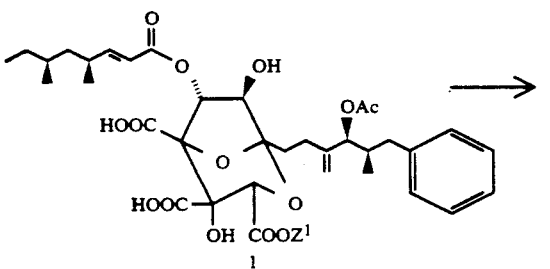
1

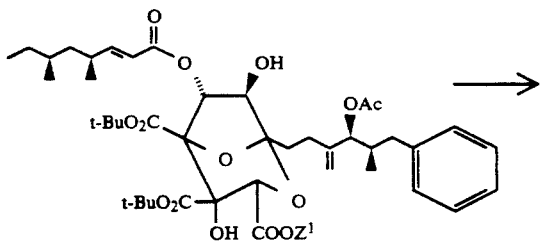
5

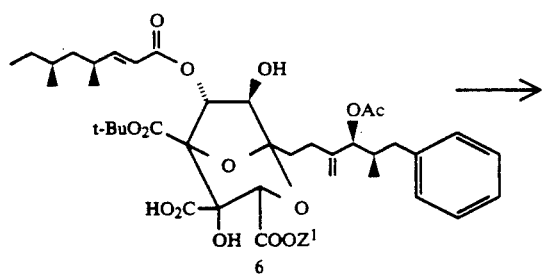
6

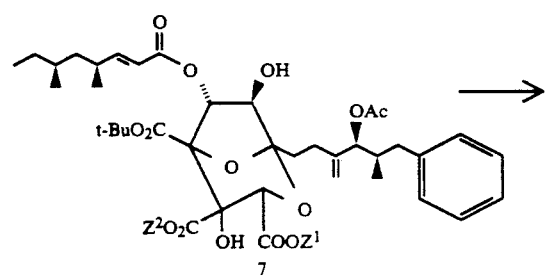
7

-continued
SCHEME C

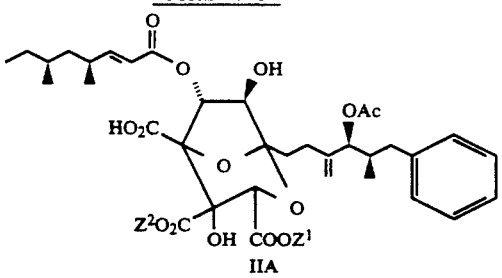
IIA

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases. They may be administered orally or parenterally in the form of a capsule, a tablet, an injectable preparation or the like. It is usually desirable to use the oral route. Active metabolites of the instant compounds are contemplated within the scope of the invention. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthase which comprises the administration to a subject in need of such treatment a nontoxic therapeutically effective amount of compound represented by structural formula (I) and pharmaceutically acceptable salts thereof. Specifically, the compounds of this invention are useful in treating disease conditions such as, but not limited to, hypercholesterolemia which result from the action of the enzyme squalene synthase. They may be administered orally or parenterally in the form of a capsule, a tablet, an injectable preparation or the like. It is usually desirable to use the oral route. Active metabolites of the instant compounds are contemplated within the scope of the invention. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N-N'-dibenzylethylendiamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene epoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Appropriate daily dosages for adults are niacin (2–8 gm), probucol (up to 1000 mg), clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The usefulness of the compounds of this invention as cholesterol lowering agents is shown by the following assay.

ORAL MOUSE ASSAY

The compound to be tested is dissolved in 5% EMULPHOR ® in 0.9% NaCl at a concentration of 24 mg/kg. The solution of the test compound is given by gavage to each mouse in a dose volume that does not exceed 0.15 ml per mouse. Six mice per group are dosed this way. After dosing of the animals, a 30 minute incubation period is allowed to elapse, and then each animal receives subcutaneously a dose of the radiolabelled tracer tritiated mevalonolactone, 0.5 microcuries, in 25 $\mu$l of saline. The tracer used is incorporated into cholesterol and the incorporation is used as a measure of in vivo cholesterol synthesis. After dosing with the tracer, another 30 minutes is allowed to elapse and then the animals are sacrificed. Upon sacrifice, each liver is removed and saponified in a solution of 40% KOH/ethyl alcohol overnight at 60° C. Next, the liver/40% KOH/ethyl alcohol mixture is extracted with petroleum ether (2×10 ml) to remove the non-saponifiables, then one half of the organic layer is counted in a liquid scintillation counter. The numbers (DPMs) observed are expressed as a percentage of the control value to obtain percent inhibition of cholesterol synthesis. The control used is the vehicle (EMULPHOR ® and saline).

Depending on the results obtained using 24 mg/kg of the compound being tested, the procedure is repeated using 12 mg/kg, 6 mg/kg, 2 mg/kg and 0.67 mg/kg, to obtain sufficient results to calculate the $ED_{50}$. Representative compounds of this invention tested in this assay demonstrated $ED_{50}$'s of less than 8 mpk.

The following Examples illustrate the preparation of the compounds of formula (I) and their incorporation into pharmaceutical compositions and as such are not to be considered as limiting the invention set forth in the claims appended hereto. The word "hour(s)" may be abbreviated herein as "hr(s)". The number-letter designations given in parenthesis after compound names in the Examples (e.g., 1a, 1b, 1c, 2a, etc.) correspond to the compounds depicted in Tables 1 and 2, above.

EXAMPLE 1

Preparation of IA-3-ethyl-4-pivaloyloxymethyl diester (1b)

Step 1: Preparation of IA-3-ethyl ester (compound 1 in Scheme A wherein $Z^1$ is ethyl)

A mixture of acetyl chloride (0.15 ml) and absolute ethanol (4 ml) was stirred for 1 hr at room temperature after which time IA was added (500 mg). The resulting mixture was stirred for 15 hrs at room temperature. The solution was concentrated in vacuo. One third of the crude product was purified by preparative high pressure liquid chromatography (HPLC) to afford the title compound as a white solid. $^1$H NMR (400 MHz, CD$_3$OD) $\delta$7.13–7.27 (m, 5H), 6.81–6.87 (dd, 1H), 6.30 (s, 1H), 5.78 (d, 1H), 5.28 (s, 1H), 5.07 (d, 1H), 5.06 (s, 1H), 5.01 (s, 1H), 4.17–4.22 (m, 2H), 4.03 (s, 1H), 2.65–2.70 (dd, 1H), 2.33–2.45 (m, 4H), 2.22–2.24 (m, 1H), 2.09 (s, 3H), 1.98–2.04 (m, 2H), 1.23–1.42 (t+m, 6H), 1.11–1.15 (m, 2H), 1.02 (d, 3H), 0.84–0.87 (m, 9H).

Step 2: Preparation of IA-3-ethyl-4-pivaloyloxymethyl diester

To a solution of the product from Step 1 (72 mg, 0.10 mmol) in 5 ml of benzene was added DBU (0.016 ml, 0.11 mmol) and chloromethyl pivalate (0.022 ml, 0.15 mmol). The mixture was stirred for 60 hrs at 45° C. The solution was concentrated in vacuo and the residue was purified by preparative TLC (thin layer chromatography) then by preparative HPLC to give the title compound. $^1$H NMR (400 MHz, CD$_3$OD) $\delta$7.16–7.26 (m, 5H), 6.80–6.87 (dd, 1H), 6.11 (s, 1H), 5.89–5.90 (d, 1H), 5.83–5.84 (d, 1H), 5.77–5.81 (d, 1H), 5.21 (s, 1H), 5.07 (d, 1H), 5.01 (s, 1H), 4.95 (s, 1H), 4.14–4.24 (m, 2H), 4.02 (s, 1H), 2.68 (dd, 1H), 2.39–2.48 (m, 3H), 2.28–2.36 (m,1H), 2.18–2.26 (m, 1H), 2.09 (s, 3H), 1.98–2.03 (m, 2H), 1.20–1.42 (s+t+m, 15H), 1.10–1.16 (m, 2H), 1.02 (d, 3H), 0.85–0.88 (m, 9H). MS, FAB(−) m/e 831 (m+−1).

By the method described in Scheme A and Example 1, the following compounds described in Examples 2–17 were prepared.

EXAMPLE 2

IA-3-ethyl-4-(1-pivaloyloxy)ethyl diester (1 h)

$^1$H NMR (400 MHz, CD$_3$OD) $\delta$6.91–7.02 (q, 1H), 6.76–6.88 +6.78–6.90 (dd+dd, 1H, 3:1), 6.12+6.29 (d+d, 1H, 3:1), 5.22+5.16 (s+s, 1H, 3:1), 3.99+4.03 (d+d, 1H, 3:1), 1.53 (d, 3H). MS, FAB(−) m/e 845 (m+−1).

EXAMPLE 3

IA-3-ethyl-4-(1-ethoxycarbonyloxy)ethyl diester (1f)

$^1$H NMR (400 MHz, CD$_3$OD) $\delta$6.81–6.87 (m, 2H), 6.12+6.24 (d+d, 1H, 4:1), 5.22+5.18 (s+s, 1H, 4:1), 4.01+4.05 (d+d, 1H, 4:1), 1.57+1.62 (d+d, 3H, 4:1). MS, FAB(−) m/e 833 (m+−1).

EXAMPLE 4

IA-3-ethyl-4-(3-phthalidyl) diester (1j)

$^1$H NMR (400 MHz, CD$_3$OD) $\delta$7.91 (d, 1H), 7.79 (s, 2H), 7.70–7.75 (m, 1H), 7.55 (s, 1H), 7.11–7.26 (m, 5H), 6.84–6.90 (dd, 1H), 6.26 (d, 1H), 5.80 (d, 1H), 5.31 (s, 1H), 5.06 (d, 1H), 5.00 (s, 1H), 4.96 (s, 1H), 4.23–4.32 (m, 2H), 4.06 (d, 1H), 2.64–2.70 (dd, 1H), 2.38–2.50 (m, 3H), 2.28–2.37 (m, 1H), 2.17–2.27 (m, 1H), 2.09 (s, 3H), 2.00–2.04 (m, 2H), 1.24–1.42 (t+m, 6H), 1.08–1.18 (m, 2H), 1.01 (d, 3H), 0.81–0.86 (m, 9H). MS, FAB(−) m/e 849 (m+ −1).

EXAMPLE 5

IA-3-ethyl-4-(5′-methyl-2′-oxo-1′3′-dioxolen-4′-yl)methyl diester (1l′)

$^1$H NMR (400 MHz, CD$_3$OD) δ7.11–7.26 (m, 5H), 6.83–6.89 (dd, 1H), 6.14 (d, 1H), 5.85 (d, 1H), 5.17 (s, 1H), 5.00–5.10 (m, 5H), 4.12–4.20 (q, 2H), 4.01 (d, 1H), 2.67–2.72 (dd, 1H), 2.30–2.52 (m, 4H), 2.18–2.28 (m, 1H), 2.18 (s, 3H), 2.09 (s, 3H), 2.00–2.07 (m, 2H), 1.26–1.42 (m, 3H), 1.20 (t, 3H), 1.08–1.17 (m, 2H), 1.01 (d, 3H), 0.84–0.87 (m, 9H). MS, FAB(−) m/e 829 (m+ −1).

EXAMPLE 6

IA-3-methyl ester $^1$H NMR (400 MHz, CD$_3$OD) δ7.29–7.09 (m, 5H), 6.85 (dd, J=15.6, 8.5 Hz, 1H), 6.31 (d, J=1.8 Hz, 1H), 5.80 (d, J=15.6 Hz, 1H), 5.31 (s, 1H), 5.09 (d, J=4.9 Hz, 1H), 5.03 (s, 1H). 4.98 (s, 1H), 4.02 (d, J=1.7 Hz, 1H), 3.72 (s, 3H), 2.70 (m, 1H), 2.45 (m, 3H), 2.36–2.21 (m, 3H), 2.05 (s, 3H), 1.45–1.26 (m, 6H), 1.19–1.10 (m, 3H), 1.05 (d, J=6.4 Hz, 3H), 0.91–0.82 (m, 10H), MS data (FAB) 685 (M+Na)+.

EXAMPLE 7

IA-3-methyl-4-pivaloyloxymethyl diester (1a)

$^1$H NMR (400 MHz, CD$_3$OD) δ7.13–7.27 (m, 5H), 6.82–6.88 (dd, 1H), 6.12 (s, 1H), 5.90–5.91 (d, 1H), 5.79–5.83 (d, 2H), 5.23 (s, 1H), 5.06 (d, 1H), 5.03 (s, 1H), 4.96 (s, 1H), 4.02 (s, 1H), 3.72 (s, 3H), 2.66 (dd, 1H), 2.26–2.38 (m, 1H), 2.19–2.26 (m, 1H), 2.09 (s, 3H), 1.91–2.04 (m, 2H), 1.29–1.35 (m, 3H), 1.22 (s, 9H), 1.10–1.17 (m, 2H), 1.01 (d, 3H), 0.84–0.87 (m, 9H). MS, FAB(−) m/e 818.3 (m+ −1).

EXAMPLE 8

IA-3-isopropyl ester $^1$H NMR (200 MHz, CD$_3$OD) δ7.30–7.10 (m, 5H), 6.86 (dd, J=8, 16 Hz, 1H), 6.31 (d, J=1.7 Hz, 1H), 5.80 (d, J=16 Hz, 1H), 5.26 (s, 1H), 5.10 (d, J=4.6 Hz, 1H), 5.04 and 5.00 (ea s, ea 1H), 4.11 (t, J=7 Hz, 2H), 4.03 (d, J=1.8 Hz, 1H), 2.68 (m, 1H), 2.52–2.10 (m), 2.10 (s, 3H), 1.40–1.10 (m), 1.24 (d, J=7 Hz, 6H), 1.01 (d, J=7 Hz, 3H), 0.90–0.75 (m).

EXAMPLE 9

IA-3-isopropyl-4-pivaloyloxymethyl diester (1e)

$^1$H NMR (400 MHz, CD$_3$OD) δ7.12–7.27 (m, 5H), 6.80–6.87 (dd, 1H), 6.10 (d, 1H), 5.91 (d, 1H), 5.85 (d, 1H), 5.78 (d, 1H), 5.18 (s, 1H), 5.07 (d, 1H), 4.95–5.00 (2s, 3H), 4.02 (d, 1H), 2.64–2.70 (dd, 1H), 2.40–2.46 (m, 3H), 2.28–2.36 (m, 1H), 2.18–2.26 (m, 1H), 2.09 (s, 3H), 1.98–2.04 (m, 2H), 1.19–1.41 (s+d+m, 18H), 1.09–1.16 (m, 2H), 1.01 (d, 3H), 0.84–0.87 (m, 9H). MS, FAB(−) m/e 845 (m+ −1).

EXAMPLE 10

IA-3-n-propyl ester $^1$H NMR (200 MHz, CD$_3$OD) δ7.30–7.10 (m, 5H), 6.84 (dd, J=8, 16 Hz, 1H), 6.31 (d, 1.7 Hz, 1H), 5.80 (d, J=16 Hz, 1H), 5.29 (s, 1H), 5.08 (d, J=4.6 Hz, 1H), 5.03 and 4.97 (ea s, ea 1H), 4.11 (t, J=7 Hz, 2H), 4.04 (d, J=1.8 Hz, 1H), 2.69 (m, 1H), 2.52–2.10 (m), 2.10 (s, 3H), 1.90–1.12 (m), 1.65 (q, J=7 Hz, 2H), 1.44–1.06 (m), 1.01 (d, J=7 Hz, 3H), 0.94 (t, J=7 Hz, 3H), 0.86 (m).

EXAMPLE 11

IA-3-n-propyl-4-pivaloyloxymethyl diester (1c)

$^1$H NMR (400 HMz, CD$_3$OD) δ7.13–7.26 (m, 5H), 6.85 (dd, 1H), 6.09 (d, 1H), 5.78–5.93 (d+dd, 3H), 5.22 (s, 1H), 5.07 (d, 1H), 4.99 (s, 1H), 4.96 (s, 1H), 4.10 (t, 2H), 4.02 (d, 1H), 2.69 (dd, 1H), 2.27–2.50 (m, 4H), 2.17–2.25 (m, 1H), 2.08 (s, 3H), 2.00–2.06 (m, 2H), 1.62–1.70 (m, 2H), 1.26–141 (m, 3H), 1.22 (s, 9H), 1.08–1.17 (m, 2H), 1.01 (d, 3H), 0.93 (t, 3H), 0.84–0.86 (m, 9H). MS, FAB(−) m/e 845 (m+ −1).

EXAMPLE 12

IA-3-n-propyl-4-(1-pivaloyloxy)ethyl diester (1i)

$^1$H NMR (400 MHz, CD$_3$OD) δ6.98+6.93 (q+q, 1H, 3:1), 6.12+6.28 (d+d, 1H, 3:1), 5.24+5.18 (s+s, 1H, 3:1), 4.01+4.04 (d+d, 1H, 3:1), 1.55 (t, 3H). MS, FAB(−) m/e 859 M+ −1).

EXAMPLE 13

IA-3-n-propyl-4-(1-ethoxycarbonyloxy)ethyl diester (1 g)

$^1$H NMR (400 MHz, CD$_3$OD) δ6.81–6.87 (m, 2H), 6.12+6.24 (d+d, 1H, 5:1), 5.24+5.21 (s+s, 1H, 5:1), 4.15–4.21+4.07–4.12 (m+m, 2H, 5:1), 4.01+4.05 (d+d, 1H, 5:1), 1.56+1.62 (d+d, 3H, 5:1). MS, FAB(−) m/e 847 (M+ −1).

EXAMPLE 14

IA-3-n-propyl-4-(3-phthalidyl) diester (1k)

$^1$H NMR (400 MHz, CD$_3$OD) δ7.90 (d, 1H), 7.79–7.81 (m, 2H), 7.68–7.73 (m, 1H), 7.52 (s, 1H). MS, FAB(−) m/e 863 (m+ −1).

EXAMPLE 15

IA-3-n-propyl-4-(5′-methyl-2′-oxo-1′,3′-dioxolen-4′-yl)methyl diester (1m)

$^1$H NMR (400 MHz, CD$_3$OD) δ5.23 (s, 1H), 5.15 (d, 1H), 5.07 (d, 1H), 5.00 (d, 2H), 4.96 (s, 1H). MS, FAB(−) m/e 843 (m+ −1).

EXAMPLE 16

Step 1: IC-3-ethyl ester $^1$H NMR (400 MHz, CD$_3$OD) δ4.10–4.21 (m, 2H), 1.18–1.26 (t+m, 5H). MS, FAB(−) m/e 781 (M+ −1).

Step 2: IC-3-ethyl-4-pivaloyloxymethyl diester (2a)

$^1$H NMR (400 MHz, CD$_3$OD) δ7.21–7.25 (m, 4H), 7.12–7.16 (m, 6H), 6.07 (d, 1H), 5.83–5.86 (dd, 2H), 5.27–5.42 (m, 2H), 5.17 (s, 1H), 4.14–4.24 (m, 2H), 4.01 (d, 1H), 2.70–2.75 (dd, 1H), 2.53–2.58 (m, 2H), 2.25–2.37 (t+m, 5H), 2.00–2.11 (m, 2H), 2.02 (s, 3H), 1.86–1.91 (m 2H), 1.64–1.74 (m, 2H), 1.53–1.64 (m, 4H), 1,20–1.34 (s+m, 15H), 0.92 (d, 3H), MS, FAB(−) m/e 895 (m+ −1).

EXAMPLE 17

Step 1: IC-3-n-propyl ester $^1$H NMR (400 MHz, CD$_3$OD) δ4.04 (t, 2H), 1.50–1.68 (m, 8H), 0.86–0.90 (m, 6H). MS, FAB(−) m/e 795 (M+ −1).

Step 2: IC-3-n-propyl-4-pivaloyloxymethyl diester (2b)

$^1$H NMR (400 MHz, CD$_3$OD) δ7.20–7.25 (m, 4H), 7.12–7.15 (m, 6H), 6.04 (d, 1H), 5.81–5.87 (dd, 2H), 5.26–5.42 (m, 2H), 5.16 (s, 1H), 4.07 (t, 2H), 3.97 (d, 1H), 2.70–2.76 (dd, 1H), 2.55 (td, 2H), 2.26–2.36 (m, 5H), 1.97–2.10 (m, 2H), 2.00 (s, 3H), 1.84–1.89 (m, 2H), 1.52–1.68 (m, 8H), 1.20–1.32 (m, 3H), 1.17 (s, 9H), 0.90–0.94 (m, 6H), 0.84 (d, 3H). MS, FAB(−) m/e 909 (m+ −1).

The following was prepared according to the method described in Scheme B.

EXAMPLE 18

Preparation of IA-3-allyl-4-pivaloyloxymethyl diester (Id)

Step 1: Preparation of IA-3-benzyl ester

The title compound was prepared by the procedure described in Example 1, Step 1. $^1$H NMR (300 MHz, CD$_3$OD) δ7.46–7.12 (m, 10H), 6.88 (dd, J=8.9, 18 Hz, 1H), 6.38 (brs, 1H), 5.84 (d, J=15 Hz, 1H), 5.42 (s, 1H), 5.23 (dd, J=13, 51 Hz, 2H), 5.14 (s, 1H), 5.04 and 5.00 (2s, 2H), 4.06 (br s, 1H), 2.71 (m, 1H), 2.54–2.00 (m, 7H), 2.12 (s, 3H), 1.50–1.1 (m, 6H), 1.07 (d, J=6 Hz, 3H), 0.90 (m, 9H); FAB m/e 793 (M+2Li), 799 (M+3Li).

Step 2: Preparation of IA-3-benzyl-4,5-di-t-butyl triester

To a solution of IA-3-benzyl ester (100 mg) in methylene chloride (2 mL) was added O-t-butyl-N, N'-diisopropylisourea (300 mg) and the solution was stirred at 40° C. for 2 days. The reaction mixture was then cooled to room temperature, concentration in vacuo and filtered through silica eluting with ethyl acetate:hexane, 1:4 to yield the title compound. $^1$H NMR (400 MHz, CDCl$_3$) δ7.35–7.08 (m, 10H), 6.89 (dd, J=16, 8.4 Hz, 1H), 5.97 (d, J=1 Hz, 1H), 5.75 (d, J=16 Hz, 1H), 5.24 (s, 1H), 5.16 (dd, J=12 Hz, 2H), 5.06 (br s, 1H), 4.94 (br s, 2H), 4.00 (br s, 1H), 2.96 (d, J=2 Hz, 1H), 2.66 (m, 1H), 2.5–2.2 (m, 5H), 2.15–2.00 (m, 4H), 2.05 (s, 3H), 1.39 (s, 9H), 1.37 (s, 9H), 1.40–1.05 (m, 6H), 1.02 (d, J=6 Hz, 3H), 0.86–0.76 (m, 9H).

Step 3: Preparation of IA-4,5-di-t-butyl-diester

To a solution of IA-3-benzyl-4,5-di-t-butyl triester (100 mg) in methanol (4 mL) was added 1-methyl-1,4-cyclohexadiene (200 μL) and Pd/C (50 mg). The reaction mixture was stirred at 30°–35° C. for 1.5 hr and filtered over celite. The filtrate was evaporated in vacuo to give the title compound. $^1$H NMR (400 MHz, CD$_3$OD) δ7.30–7.10 (m, 5H), 6.89 (dd, J=8.16 Hz, 1H), 6.43 (d, J=1 Hz, 1H), 5.82 (d, J=16 Hz, 1H), 5.06 (d, J=5 Hz, 1H), 5.04 (s, 1H), 5.01 and 4.96 (each s, each 1H), 4.07 (s, 1H), 2.69 (m, 1H), 2.5–2.20 (m, 6H), 2.10 (s, 3H), 1.60 (s, 9H), 1.42 (s, 9H), 1.65–1.05 (m, 6H), 1.03 (d, J=8.1 Hz, 3H), 0.88 (m, 10H).

Step 4: Preparation of IA-3-allyl-4,5-di-t-butyl triester

To the IA-4,5-di-t-butyl diester (200 mg, 0.25 mmol) in benzene (3 ml) was added DBU (0.074 ml, 0.5 mmol) and allyl bromide (0.043 ml, 0.5 mmol). The resulting mixture was stirred overnight at room temperature. The solution was filtered and concentrated. The product was purified by preparative TLC (25% EtOAc in hexane) to give 88 mg of the title compound. $^1$H NMR (200 MHz, CDCl$_3$) δ7.04–7.24 (m, 5H), 6.80–6.92 (dd, 1H), 5.95 (dd, 1H), 5.68–5.90 (d+m, 2H), 5.10–5.29 (m, 2H), 5.17 (s, 1H), 5.04 (d, 1H), 4.90 (s, 2H), 4.49–4.68 (m, 2H), 3.96–4.02 (s+broad s, 2H), 3.03 (d, 1H), 2.60–2.70 (dd, 1H), 2.25–2.46 (m, 5H), 1.98–2.12 (s+m, 5H), 1.48 (s, 9H), 1.36 (s, 9H), 1.02–1.36 (m, 5H), 0.96 (d, 3H), 0.72–0.80 (m, 9H). MS, FAB(−) m/e 801 (m+ −1−C$_3$H$_4$).

Step 5: Preparation of IA-3-allyl ester

To the product from Step 1 (160 mg) in CH$_2$Cl$_2$ (10 ml) was added TFA (0.9 ml). The mixture was stirred overnight at room temperature. The solution was concentrated. The residue was flashed with 2×2 ml of toluene to get rid of the trace amount of TFA. The product was purified by preparative reverse phase HPLC to afford 134 mg of the title compound. $^1$H NMR (200 HMz, CD$_3$OD) δ7.10–7.26 (m, 5H), 6.76–6.88 (dd, 1H), 6.28 (d, 1H), 5.72–5.93 (d+m, 2H), 5.15–5.37 (s+m, 3H), 5.04 (d, 1H), 4.98 (s, 1H), 4.93 (s, 1H), 4.58–4.65 (m, 2H), 3.99 (d, 1H), 2.58–2.70 (dd, 1H), 2.12–2.48 (m, 5H), 1.92–2.08 (s+m, 5H), 1.02–1.36 (m, 5H), 0.96 (d, 3H), 0.77–0.84 (m, 9H).

Step 6: Preparation of IA-3-allyl-4-pivaloyloxymethyl diester

The title compound was prepared from the product of Step 2, above, according to the procedure described in Example 1, Step 2. $^1$H NMR (200 MHz, CD$_3$OD) δ7.10–7.23 (m, 5H), 6.76–6.88 (dd, 1H), 6.11 (dd, 1H), 5.72–5.94 (d+dd+m, 4H), 5.17–5.36 (s+m, 3H), 5.03 (d, 1H), 4.98 (s, 1H), 4.95 (s, 1H), 4.58–4.64 (m, 2H), 3.98 (d, 1H), 2.58–2.68 (dd, 1H), 2.11–2.33 (m, 5H), 2.09 (s, 3H), 1.92–2.10 (m, 2H), 1.06–1.41 (s+m, 14H), 0.97 (d, 3H), 0.76–0.85 (m, 9H). MS, FAB(−) m/e 843 (m+ −1).

EXAMPLE 19

As a specific embodiment of an oral composition of a compound of this invention, 20 mg of the compound 1b from Example 1 is formulated with sufficient finely divided lactose to provide a total amount of 580 to 590 mg to fill a size 0 hard gelatin capsule.

EXAMPLE 20

Preparation of an Ammonium Salt

A 0.1 mmol sample of the free acid of a compound of formula (I) is dissolved in 10 mL of ethyl acetate. The resulting solution is saturated with gaseous ammonia upon which the ammonium salt precipitates from solution.

EXAMPLE 21

Preparation of a Potassium Salt

A solution of 0.1 mmol of the free acid of a compound of formula (I) in 10 mL of methanol is treated with an aqueous or methanolic solution containing 0.1 mmol of potassium hydroxide. Evaporation of the solvent affords the potassium salt.

In a similar fashion the sodium and lithium salts can be formed.

EXAMPLE 22

Preparation of a Calcium Salt

A solution of 0.1 mmol of the free acid of a compound of formula (I) in 20 mL 6:4 methanol/water is treated with an aqueous solution of 0.1 mmol of calcium hydroxide. The solvents are evaporated to give the corresponding calcium salt.

EXAMPLE 23

Preparation of an Ethylenediamine Salt

A solution of 0.1 mmol of the free acid of a compound of formula (I) in 10 mL 6:4 methanol is treated with 0.1 mmol of ethylenediamine. Evaporation of the solvent affords the ethylenediamine salt.

EXAMPLE 24

Preparation of a Tris(hydroxymethyl)aminomethane Salt

To a solution of 0.1 mmol of the free acid of a compound of formula (I) in 10 mL of methanol is added from 0.1 to 0.3 mmol of tris(hydroxymethyl)-aminomethane dissolved in 10 mL of methanol. Evaporation of the solvent gives a corresponding salt form of the exact composition of which is determined by the molar ratio of amine added. Similarly prepared are the salts of L-ornithine, L-lysine, and N-methylgluacamine.

EXAMPLE 25

Preparation of an L-arginine Salt

A solution of 0.1 mmol of the free acid of a compound of formula (I) in 10 mL of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglucamine.

The following was prepared according to the method described in Scheme C.

EXAMPLE 26

Preparation of IA-3-n-propyl-4-pivaloyloxymethyl diester (Ic)

Step 1: Preparation of IA-3-n-propyl-4,5-di-butyl triester

A solution of 1-propanol (7.5 ml) and acetyl chloride (0.18 ml) was stirred for 1 hr at room temperature to which was added IA (2.5 g). The resulting mixture was stirred overnight at room temperature. The solution was concentrated. The residue was dissolved in 20 ml of CH$_2$Cl$_2$ and added O-t-butyl-N,N'-diisopropylisourea (8 g) was added. After stirring overnight at room temperature, the solution was filtered and concentrated. The residue was purified by flash chromatography on silica gel (25% EtOAC in hexane) to yield the title compound. $^1$H NMR (200 MHz, CDCl$_3$) δ7.07–7.22 (m, 5H), 6.80–6.92 (dd, 1H), 5.97 (d, 1H), 6.72 (d, 1H), 5.17 (s, 1H), 5.05 (d, 1H), 4.91 (s, 2H), 3.97–4.12 (d+m, 4H), 3.18 (br s, 1H), 2.60–2.69 (dd, 1H), 2.25–2.45 (m, 4H), 1.98–2.12 (s+m, 6H), 1.48–1.67 (s+m, 11H), 1.42 (s, 9H), 1.03–1.31 (m, 5H), 0.98 (d, 3H), 0.72–0.86 (m, 12H).

Step 2: Preparation of IA-3-n-propyl-5-t-butyl diester

To the product of Step 1, above, (1 g) in THF (20 ml) was added thionyl chloride (3.45 ml). After stirring overnight at room temperature, the solution was concentrated. The residue was dissolved in di-ethyl ether (40 ml) and poured into 50 ml of saturated NaHCO$_3$ solution. The ether phase was separated, dried and concentrated. The residue was purified by preparative TLC (8% MeOH in CH$_2$Cl$_2$) to afford the title compound. $^1$H NMR (200 MHz, CD$_3$OD) δ7.10–7.27 (m, 5H), 6.69–6.81 (dd, 1H), 6.56 (br s, 1H), 5.78 (d, 1H), 5.34 (s, 1H), 5.05 (d, 1H), 4.96 (s, 1H), 4.92 (s, 1H), 4.04 (t, 2H), 3.95 (d, 1H), 2.67 (dd, 1H), 2.16–2.52 (m, 5H), 2.04 (s, 3H), 1.86–2.00 (m, 2H), 1.56–1.68 (m, 2H), 1.04–1.40 (s+m, 14H), 0.97 (d, 3H), 0.88 (t, 3H), 0.78–0.84 (m, 9H).

Step 3: Preparation of IA-3-n-propyl-4-pivaloyloxymethyl diester

To the product of Step 2, above, (0.5 g) in CH$_3$CN (10 ml) was added DBU (0.14 ml) and chloromethyl pivalate (0.14 ml). The mixture was refluxed overnight. The solution was filtered and concentrated. The residue was purified by preparative TLC (25% EtOAc in hexane) to give IA-3-propyl-4-pivaloyloxymethyl-5-t-butyl triester. The product was then dissolved in 10 ml of CH$_2$Cl$_2$ and TFA (1.6 ml) was added. The mixture was stirred overnight at room temperature. The solution was concentrated and flashed with 3×3 ml of toluene. The residue was purified by preparative TLC (8% MeOH in CH$_2$Cl$_2$) then by preparative HPLC to yield the title compound. $^1$H NMR (400 MHz, CD$_3$OD) δ7.13–7.26 (m, 5H), 6.85 (dd, 1H), 6.09 (d, 1H), 5.78–5.93 (d+dd, 3H), 5.22 (s, 1H), 5.07 (d, 1H), 4.99 (s, 1H), 4.96 (s, 1H), 4.10 (t, 2H), 4.02 (d, 1H), 2.69 (dd, 1H), 2.27–2.50 (m, 4H), 2.17–2.25 (m, 1H), 2.08 (s, 3H), 2.00–2.06 (m, 2H), 1.62–1.70 (m, 2H), 1.26–141 (m, 3H), 1.22 (s, 9H), 1.08–1.17 (m, 2H), 1.01 (d, 3H), 0.93 (t, 3H), 0.84–0.86 (m, 9H). MS, FAB(−) m/e 845 (m+ −1).

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A compound of structural formula (I):

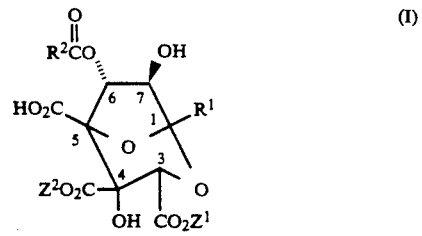

wherein:
R$^1$ is
(1)

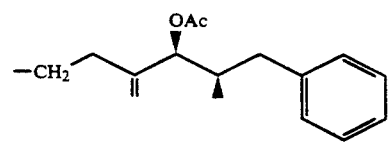

or
(2)

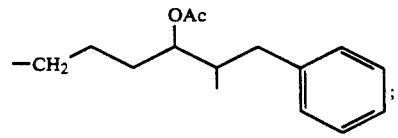

R$^2$ is
(1)

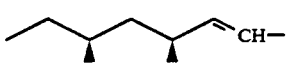

or (2)

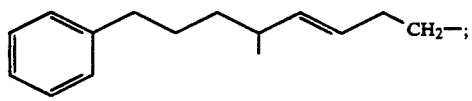

$Z^1$ is $C_{1-3}$alkyl or —$CH_2$—CH=$CH_2$;
$Z^2$ is (1)

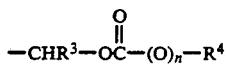

wherein
$R^3$ is —H or $C_{1-4}$alkyl,
n is zero or 1, and
$R^4$ is
  a) $C_{1-5}$ alkyl,
  b) phenyl, or
  c) phenyl substituted with X and Y, defined below,
or, when $R^3$ is $C_{1-4}$ alkyl, $R^3$ and $R^4$ are joined together to form a monocyclic or bicyclic ring system,
or, $R^4$ is joined together with the carbon to which $R^3$ is attached to form a monocyclic or bicyclic ring system, and $R^3$ represents the bond between $R^4$ and the carbon to which $R^3$ is attached, (2)

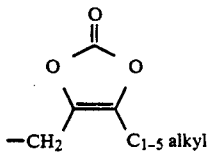

or (3)

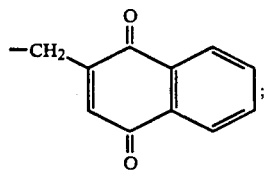

and
X and Y are each independently selected from:
(1) hydrogen,
(2) hydroxy,
(3) halogen,
(4) trifluoromethyl,
(5) $C_{1-4}$alkyl,
(6) $C_{1-4}$alkyl—O—,
(7) $C_{1-4}$alkyl—C(O)—O—,
(8) —$CO_2C_{1-4}$alkyl,
(10) —$CO_2H$, and

(11) nitro;
or a pharmaceutically acceptable salt thereof.

2. The compound of claim 1 having structural formula (II):

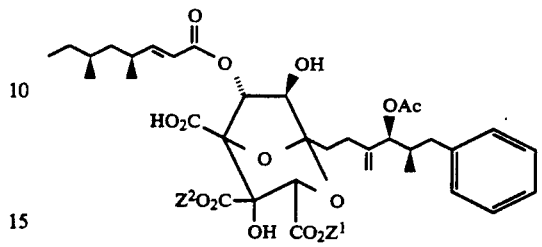 (II)

selected from the group consisting of those wherein:
a) $Z^1$ is $CH_3$ and $Z^2$ is

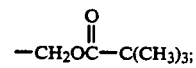

b) $Z^1$ is —$CH_2CH_3$ and $Z^2$ is

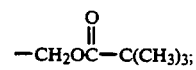

c) $Z^1$ is —$CH_2CH_2CH_3$ and $Z^2$ is

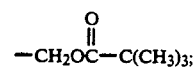

d) $Z^1$ is —$CH_2$—CH=$CH_2$ and $Z^2$ is

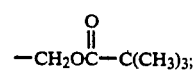

e) $Z^1$ is —$CH(CH_3)_2$ and $Z^2$ is

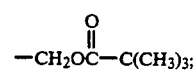

f) $Z^1$ is —$CH_2CH_3$ and $Z^2$ is

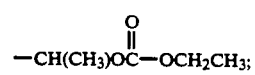

g) $Z^1$ is —$CH_2CH_2CH_3$ and $Z^2$ is

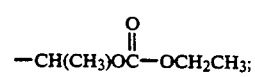

h) $Z^1$ is —$CH_2CH_3$ and $Z^2$ is

i) $Z^1$ is —$CH_2CH_2CH_3$ and $Z^2$ is

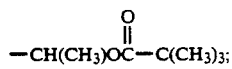

j) $Z^1$ is —$CH_2CH_3$ and $Z^2$ is

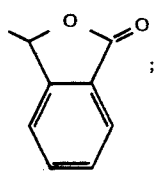

k) $Z^1$ is —$CH_2CH_2CH_3$ and $Z^2$ is

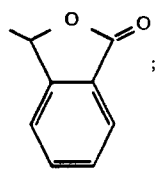

l') $Z^1$ is —$CH_2CH_3$ and $Z^2$ is

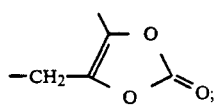

and
m) $Z^1$ is —$CH_2CH_2CH_3$ and $Z^2$ is

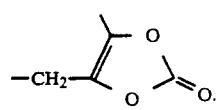

3. The compound of claim 1 having structural formula (III):

selected from the group consisting of those wherein:
a) $Z^1$ is —$CH_2CH_3$ and $Z^2$ is

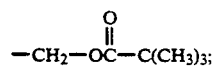

and
b) $Z^1$ is —$CH_2CH_2CH_3$ and $Z^2$ is

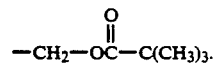

4. A pharmaceutical composition comprising a nontoxic therapeutically effective amount of a compound of claim 1 and a pharmaceutically acceptable carrier.

5. A pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

6. A pharmaceutical composition comprising a nontoxic therapeutically effective amount of a compound of claim 1 in combination with a nontoxic therapeutically effective amount of a cholesterol lowering agent selected from the group consisting of:
  (a) HMG-CoA reductase inhibitor;
  (b) HMG-CoA synthase inhibitor;
  (c) squalene exposidase inhibitor;
  (d) probucol;
  (e) niacin;
  (f) gemfibrozil; and
  (g) clofibrate.

7. The composition of claim 6 wherein the composition comprises a compound of claim 1 and an HMG-CoA reductase inhibitor.

8. The composition of claim 7 wherein the HMG-CoA reductase inhibitor is selected from lovastatin, simvastatin, pravastatin and fluvastatin.

9. A method of treating hypercholesterolemia comprising the administration to a subject in need of such treatment a nontoxic therapeutically effective amount of the compound of claim 1.

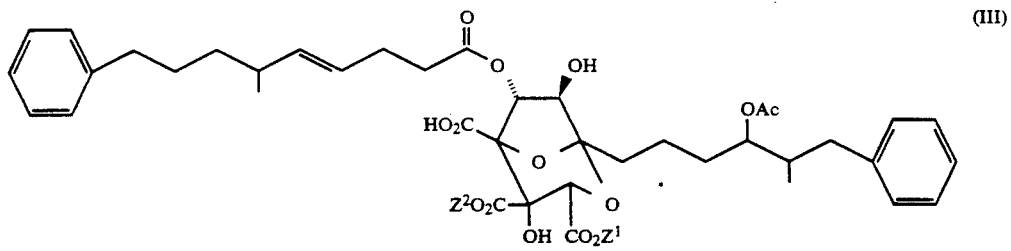

(III)

10. A method of inhibiting squalene synthase comprising the administration to a subject in need of such treatment a nontoxic therapeutically effective amount of a compound of claim 1.

* * * * *